United States Patent
Neu et al.

(10) Patent No.: US 7,612,229 B2
(45) Date of Patent: Nov. 3, 2009

(54) INDUSTRIAL PROCESS FOR THE SYNTHESIS OF 2-SUBSTITUTED 1-(HYDROXY-ETHYLIDENE)-1,1-BISPHOSFI-CONIC ACIDS OF HIGH PURITY AND THE SALTS THEREOF

(75) Inventors: Jozsef Neu, Budapest (HU); Janos Fischer, Budapest (HU); Tamas Fodor, Budapest (HU); Jozsef Törley, Budapest (HU); Tibor Gizur, Budapest (HU); Sandor Levai, Biatorbagy (HU); Adam Demeter, Budapest (HU); Eva Perenyi, Budapest (HU)

(73) Assignee: Richter Gedeon Vegyeszeti Gyar Rt., Budapest (HU)

( * ) Notice: Subject to any disclaimer, the term of this patent is extended or adjusted under 35 U.S.C. 154(b) by 508 days.

(21) Appl. No.: 10/541,866

(22) PCT Filed: Jan. 27, 2004

(86) PCT No.: PCT/HU2004/000009
§ 371 (c)(1), (2), (4) Date: Jul. 8, 2005

(87) PCT Pub. No.: WO2004/067541
PCT Pub. Date: Aug. 12, 2004

(65) Prior Publication Data
US 2006/0122395 A1    Jun. 8, 2006

(30) Foreign Application Priority Data
Jan. 28, 2003    (HU) ..................... 0300227

(51) Int. Cl.
*C07F 9/22*    (2006.01)
(52) U.S. Cl. .......................... 562/13; 546/22
(58) Field of Classification Search ............. 562/13; 546/22
See application file for complete search history.

(56) References Cited

U.S. PATENT DOCUMENTS

| | | | |
|---|---|---|---|
| 4,407,761 A | 10/1983 | Blum et al. | |
| 4,687,767 A | 8/1987 | Bosies et al. | |
| 4,922,007 A * | 5/1990 | Kieczykowski et al. | 562/13 |
| 4,990,503 A | 2/1991 | Isomura et al. | |
| 5,019,651 A | 5/1991 | Kieczykowski | |
| 5,039,669 A | 8/1991 | Isomura et al. | |
| 5,039,819 A * | 8/1991 | Kieczykowski | 548/415 |
| 5,159,108 A * | 10/1992 | Kieczykowski | 562/13 |
| 5,466,682 A * | 11/1995 | Rosini et al. | 514/76 |
| 5,908,859 A | 6/1999 | Cullinan et al. | |
| 5,908,959 A * | 6/1999 | Kubela et al. | 562/13 |
| 6,201,148 B1 * | 3/2001 | Lidor-Hadas et al. | 562/13 |
| 6,410,520 B2 * | 6/2002 | Cazer et al. | 514/89 |
| 6,573,401 B1 * | 6/2003 | Boschi Llado et al. | 562/13 |
| 7,009,071 B2 * | 3/2006 | Dabak et al. | 562/13 |
| 2004/0152916 A1 * | 8/2004 | Dabak et al. | 562/13 |
| 2004/0192655 A1 * | 9/2004 | Lifshitz-Liron et al. | 514/89 |
| 2006/0122395 A1 * | 6/2006 | Neu et al. | 546/22 |
| 2006/0293524 A1 * | 12/2006 | Patel et al. | 546/22 |

FOREIGN PATENT DOCUMENTS

| | | |
|---|---|---|
| DE | 27 02 631 | 7/1978 |
| EP | 462 663 | 12/1991 |
| EP | 494 844 | 7/1992 |
| EP | 1 205 484 | 5/2002 |
| HU | 205 766 | 5/1990 |
| HU | 211 908 | 8/1995 |
| WO | WO 98 34 940 | 8/1998 |
| WO | WO 01/10874 | 2/2001 |

OTHER PUBLICATIONS

"Prepartion of (4-Amino-1-Hydroxybutilidene . . . " by G.R. Kieczykowski et al. (J. Org.Chem 1995, 60).
"Phosphonylation by Tetraphosphorus Hexoxide" by U. Schülke (Phosphorus, Sulfur and Silicon, 1990).

* cited by examiner

*Primary Examiner*—Shailendra Kumar
(74) *Attorney, Agent, or Firm*—Jonathan Myers; Andrew Wilford

(57) ABSTRACT

Process for the synthesis of high purity 2-substituted-1-(hydroxy-ethylidene)-1,1-bisphosphonic acid of formula (I), the salts and hydrates thereof—wherein the meaning of R is 3'-pyridyl or 2'-amino-ethylidene group—from compounds of formula (II)—wherein the meaning of R is as described above—or salts and hydrates thereof with phosphorous acid in the presence of methanesulfonic acid using phosphorus pentoxide as reagent and in given case the obtained acid is converted into a salt with base.

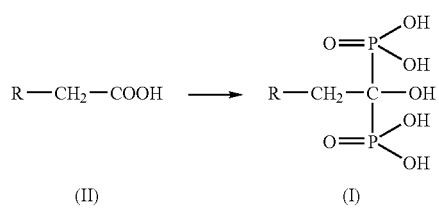

5 Claims, No Drawings

INDUSTRIAL PROCESS FOR THE SYNTHESIS OF 2-SUBSTITUTED 1-(HYDROXY-ETHYLIDENE)-1,1-BISPHOSFICONIC ACIDS OF HIGH PURITY AND THE SALTS THEREOF

CROSS REFERENCE TO RELATED APPLICATIONS

This application is the U.S. national phase of PCT application PCT/HU2004/000009 filed 27 Jan. 2004 with a claim to the priority of Hungarian patent application P0300227 itself filed 28 Jan. 2003.

The invention relates to an industrial process for the synthesis of 2-substituted 1-(hydroxy-ethylidene)-1,1-bisphosphonic acids of formula (I), the salts and hydrates thereof,—wherein the meaning of R is 3'-pyridyl or 2'-amino-ethylidene group—by phosphonylation of compounds of formula (II) or salts thereof—wherein the meaning of R is as described above.

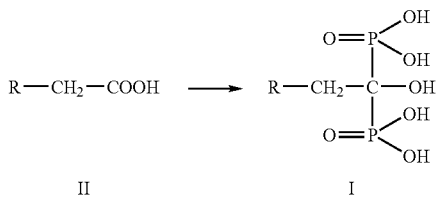

The compounds of formula (I) are known to have significant biological activity, they are active ingredients of modern drugs for treating osteoporosis. If the meaning of R in formula (I) is 3'-pyridyl group, the name of the active ingredient is risedronic acid and if the meaning of R is 2'-amino-ethylidene group the name is alendronic acid.

U.S. Pat. No. 4,407,761 (Henkel) and U.S. Pat. No. 4,621,077 (Instituto Gentili) describe the synthesis of 4-amino-1-(hydroxy-butylidene)-1,1-bisphosphonic acid by reacting 4-amino-butyric acid with phosphorous acid and phosphorus trichloride or phosphorus pentachloride or phosphorus oxychloride at 100° C. and hydrolyzing the obtained intermediate.

According to another method of U.S. Pat. No. 4,407,761 the phosphorus trichloride is added very slowly at isothermal reaction temperature above boiling point. During the process the reaction mixture doesn't remain homogenous, stirring is difficult because of heterogeneous solidifications, therefore "hot spots" are developed, which cause safety problems and variable yields, (45% and 56%). The obtained product is characterized only by melting point and molecular weight, purity data are not given. This process is not applicable for industrial scale production.

U.S. Pat. No. 4,705,651 (Instituto Gentili) tried to solve this problem by dissolution of 4-amino-butyric acid in phosphoric acid and phosphonylation thereof with phosphorus trichloride. The product of formula (I) is obtained after 6 hours reflux in 64% yield. The disadvantages of this process are that no solvent is used, so solid polymer can be formed and during the reaction strongly acidic and corrosive hydrochloric acid is evolved.

According to the method described in EP 402152 (HU 211908, Merck) 4-amino-butyric acid is dissolved in methanesulfonic acid and phosphonylated with a mixture of phosphorous acid and phosphorus trichloride. The description warns that above 85° C., under adiabatic reaction conditions the mixture becomes uncontrollably exothermic, which is accompanied by high pressure and therefore is not safe.

The optimum temperature of phosphonylation reactions using phosphorus trichloride is at 90° C. or higher temperature.

EP 402152 (HU 211908) describes that this temperature is in the adiabatic self-heat range and the use of phosphorus trichloride at 90° C. or higher temperature is not safe. The adiabatic reaction condition means, that practically there is no heat exchange between the reaction mixture and the surroundings and therefore the reaction is not controllable. Considering the above-mentioned facts, this procedure is not applicable for industrial scale production. Further disadvantage of the process is, that during the reaction strongly acidic and corrosive hydrochloric acid is evolved, which requires special and expensive equipment.

U.S. Pat. No. 5,019,651 (Merck) describes that the desired stoichiometric ratios are achieved by adding phosphorus trichloride below their boiling point: i.e. below 71° C. and the yield optimization is carried out by temperature programming. The yields are variable (64% and 90%), purity data are not given. Further disadvantage of the process is, that during the reaction strongly acidic and corrosive hydrochloric acid is evolved.

EP 715631 (HU 217 362, Merck) describes that the phosphonylation reaction is carried out in a continuous stirred tank reactor. According to the description the more favourable surface/volume ratio resulted in better heat transfer and the smaller volume of the reaction mixture reduces the probability of an unexpected thermal event. The disadvantage of this process is that special and expensive equipment is required. Yield and purity data are not given in the examples. The description establishes, that during this continuous operation different dimers, oligomers and polymers can be formed, which can be present as impurities in the product. The description says that the reaction is not always reproducible, presumably because of the significant amount of by-products.

Summarizing the prior art processes: 1.5-3 mol phosphorus trichloride is used for the preparation of 1 mol 4-amino-1-(hydroxy-butylidene)-1,1-bisphosphonic acid. This means that the synthesis of 1 mol product is accompanied by the evolvement of 4.5-9 mol dry, corrosive hydrochloric acid, which has to be neutralized subsequently. The formed hydrochloric acid gas is saturated with phosphorus trichloride, the escape of it from the system is tried to minimize with an effective condensator, having a cooling medium at least −20° C. or even colder.

According to WO 01/10874 (Medichemie) this problem is solved by reacting 4-amino-butyric acid with phosphorous acid in the presence of methanesulfonic anhydride and the formed intermediate is hydrolyzed by addition of water and after neutralization the 4-amino-1-(hydroxy-butylidene)-1,1-bisphosphonic acid sodium salt is isolated. But the stability of the phosphonylating reagent mixture is not investigated. The optimum temperature of the reaction is at 65-75° C. The yields are between 65-77%, but purity data are not given. The disadvantage of this process is that the methanesulfonic anhydride reagent is very expensive.

The basis of our invention is that the compounds of formula (I) can also be synthesized by using chlorine free phosphonylating reagent.

This discovery is surprising because according to the prior art processes the mixture of methanesulfonic acid, phosphorous acid and phosphorus pentoxide was not expected to be effective phosphonylating reagent, which is thermically more stable than the known ones.

According to the above mentioned facts, the invention relates to elaboration of a new synthesis for the preparation of 2-substituted-1-(hydroxy-ethylidene)-1,1-bisphosphonic acid of formula (I), salts and hydrates thereof—wherein the meaning of R is 3'-pyridyl or 2'-amino-ethylidene group—from the compounds of formula (II)—wherein the meaning of R is as described above—or salts and hydrates thereof with phosphorous acid in the presence of methanesulfonic acid using phosphorus pentoxide as reagent and in given case the obtained acid is converted into a salt with base.

In the process according to the invention the mol ratio of methanesulfonic acid:phosphorous acid:phosphorus pentoxide in the phosphonylating reagent is preferably between 1-5:1:0.25-1.

The mol ratio of methanesulfonic acid:phosphorous acid:phosphorus pentoxide is more preferably 2.5:1:0.5.

The mol ratio of substituted alkane carboxylic acid of formula (II) and phosphorous acid in the phosphonylating reagent is between 1:2-5, preferably 1:3.

The reagent mixture of the invention having a mol ratio of methanesulfonic acid:phosphorous acid:phosphorus pentoxide 1:1:0.5 can be handled safely at 80-85° C., In contrary with the phosphonylating reagent mixture described in EP 402152 (HU 211908), in which the exothermic decomposition processes have already started at this temperature. In the case of the above mentioned reagent mixture this chemical events don't occur in half an hour at 100° C., in the case of a reagent mixture of methanesulfonic acid:phosphorous acid:phosphorus pentoxide 2.5:1:0.5 at 120° C., in the case of mol ratio of 5:1:0.5 at 130° C., therefore the phosphonylation can be carried out 30-50° C. below the critical temperature safely, in good yield.

According to the process of the invention phosphonylation of 2-substituted-1-(hydroxy-ethylidene)-1,1-bisphosphonic acids can be carried out also 50° C. below the critical temperature in good yield, safe and in large scale.

Further advantage of the invention is that electrode is not required for neutralization of hydrochloric acid, because the phosphonylation mixture doesn't contain phosphorus halogenide.

The process according to the invention is carried out between 45 and 130° C., preferably at 70-110° C.

At the end of the phosphonylation reaction the temperature of the mixture is decreased to 20-80° C., hydrolyzed with water—equivolume to methanesulfonic acid—the used methanesulfonic acid is neutralized with a base and the product of formula (I) is isolated. The hydrolyzation of the intermediates of bisphosphonylation is carried out by addition of water in 3-6 hours at 100-110° C.

The weight of the used water is preferably the same as the volume of the used methanesulfonic acid.

After hydrolyzation the reaction mixture is cooled and partially neutralized with 30-50 weight % sodium hydroxide solution. 2-substituted-1-(hydroxy-ethylidene)-1,1-bisphosphonic acid of formula (I) can be precipitated at 0-2° C. in high purity, if the mols of the used sodium hydroxide are 50-120% of the mols of methanesulfonic acid.

The advantage of this partial neutralization compared to the known pH adjustment techniques is that highly salt tolerant electrode is not required, the use of which can meet difficulties because of the obtained dense suspension both in laboratory and in industrial scale as well.

In given case high purity sodium salt is formed from 2-substituted-1-hydroxy-ethylidene)-1,1-bisphosphonic acid of formula (I) synthesized by the process of the invention by known preparative methods, preferably with aqueous sodium hydroxide solution.

Summarizing, using the process of our invention the compounds of formula (I) and salts thereof can be synthesized safely in industrial scale, in high purity, using less environment polluting reagents, without formation of dimer, oligomer and polymer by-products.

Further advantages of the process are that special equipments are not required and pH adjustment of the dense suspension obtained during the isolation is not necessary.

The process according to the invention is applicable for industrial scale production. Further advantage of the process is that stable pharmaceutical composition can be produced from the obtained high purity active ingredient (HPLC purity >99.9%).

The invention is illustrated by the following Examples.

EXAMPLE 1

Synthesis of 4-amino-1-(hydroxy-butylidene)-1,1-bisphosphonic acid (I) monohydrate Under nitrogen 48.6 ml (0.73 mol) of 98% methanesulfonic acid and 24.6 g (0.3 mol) of phosphorous acid are placed into a flask, 21.3 g (0.15 mol) of phosphorus pentoxide is added in two portions to the obtained solution and is dissolved at 70-80° C. The reaction mixture is cooled to 40° C., 10.3 g (0.1 mol) of 4-amino-butyric acid is added and the so obtained solution is stirred at 70° C. for 24 hours. Then the reaction mixture is cooled to 40-50° C., 48.6 ml of water is added dropwise and the solution is stirred at 105-110° C. for 5 hours. The mixture is cooled and partially neutralized with 60 g of 50% NaOH solution below 20° C., then it is cooled to 0-2° C. and stirred for 2 hours.

The precipitated product is filtered, washed with 2×20 ml of water, 20 ml of isopropanol and dried at 50-60° C. to give 18.1 g (0.068 mol) of the title compound in the form of monohydrate (68% yield). HPLC purity is >99%.

In given case the product is recrystallized from 21-fold volume of distilled water in 83% yield. HPLC purity is >99.9%

EXAMPLE 2

The synthesis of 4-amino-1-(hydroxy-butylidene)-1,1-bisphosphonic acid (I) monohydrate To a reactor flask under nitrogen 118.6 kg (1.23 kmol) of methanesulfonic acid and 37.9 kg (0.462 kmol) of phosphorous acid are charged and dissolved in vigorous stirring at 35-40° C. The reaction mixture is cooled to 30-35° C. and 5.0 kg (35.2 mol) of phosphorus (V) oxide is charged. After self-heating is stopped the mixture is maintained at 70° C. to dissolution of phosphorus (V) oxide and then the solution is cooled to 38-42° C.

Then 5.0 kg (35.2 mol) of phosphorus (V) oxide is charged again and after self-heating is stopped the mixture is warmed to max. 70° C. to dissolution of phosphorus (V) oxide and then the solution is cooled to 38-42° C.

Then 5.0 kg (35.2 mol) of phosphorus (V) oxide is charged again and after self-heating is stopped the mixture is warmed to max. 70° C. to dissolution of phosphorus (V) oxide and then the solution is cooled to 42-46° C.

Then 5.0 kg (35.2 mol) of phosphorus (V) oxide is charged again and after self-heating is stopped the mixture is warmed to max. 70° C. to dissolution of phosphorus (V) oxide and then the solution is cooled to 42-46° C.

Then 5.0 kg (35.2 mol) of phosphorus (V) oxide is charged again and after self-heating is stopped the mixture is warmed to max. 70° C. to dissolution of phosphorus (V) oxide and then the solution is cooled to 48-52° C.

Further 5.0 kg (35.2 mol) of phosphorus (V) oxide is charged again and after self-heating is stopped the mixture is warmed to max. 70° C. to dissolution of phosphorus (V) oxide and then the solution is cooled to 50-55° C.

Finally 5.0 kg (35.2 mol) of phosphorus (V) oxide is charged again and after self-heating is stopped the mixture is warmed to max. 70° C. to dissolution of phosphorus (V) oxide and stirred until dissolution is completed.

The total amount of phosphorus (V) oxide is 7×5.0 kg=35.0 kg (0.246 kmol)

The reaction mixture is cooled to 35-40° C. and 4.0 kg (38.76 mol) of 4-amino-butyric acid is charged.

After self-heating is stopped 4.0 kg (38.76 mol) of 4-amino-butric acid is charged again.

After self-heating is stopped 4.0 kg (38.76 mol) of 4-amino-butric acid is charged again.

After self-heating is stopped 3.9 kg (37.79 mol) of 4-amino-butric acid is charged again, after self-heating is stopped the mixture is warmed to 65-75° C. and stirred at this temperature for 24 hours.

The total amount of the charged 4-amino-butyric acid is 15.9 kg (0.154 kmol).

After completion of the reaction the nitrogen atmosphere is stopped and the mixture is cooled to 50-55° C. 154.0 liter (154.0 kg) of water is charged to the mixture in 60 minutes. Then the reaction mixture is warmed to 105-110° C. and stirred at this temperature for 5 hours. The mixture is cooled to 0-5° C. and then a solution of 54.2 kg (1.355 kmol) of sodium hydroxide in 54.0 liter (54.0 kg) of water is charged in such a rate to keep the temperature below 20° C. Then the charger is washed with 6.0 liter of water and the washing solution is charged to the reaction mixture. The mixture is cooled to 0-5° C. temperature for 5 hours to give 25.0 kg (60.7% yield) of the title compound.

EXAMPLE 3

The synthesis of 4-amino-1-(hydroxy-butylidene)-1,1-bisphosphonic acid (I) Na salt trihydrate 25.0 kg (93.63 mol) of 4-amino-1-(hydroxy-butylidene)-1,1-bishposphonic acid monohydrate is suspended in 50.0 liter (50.0 kg) of distilled water at 25° C. and a solution of 3.75 kg (93.75 mol) of sodium hydroxide in 34.0 liter (34.0 kg) of water is charged in such a rate to keep the temperature below 30° C. Then the charger is washed with 9.5 liter (9.5 kg) of water and the washing solution is charged to the reaction mixture. The mixture is warmed to 95-100° C. and stirred at this temperature to dissolution.

Then the mixture is cooled to 80-85° C., treated with 0.5 kg of charcoal, warmed to 95-100° C. and stirred at this temperature for 10 minutes. The charcoal is filtered off and washed with 9.5 liter (9.5 kg) of hot water (95-100° C.). The clear solution is cooled with stirring at 100 rpm in 140 minutes to 0-4° C. and stirred at this temperature for further 2 hours.

The precipitated crystals are centrifuged and washed with 2×24.0 liter (24.0 kg) of water and 15.0 kg (19.23 l) of technical isopropanol. The wet product is dried in 5-15 kPa vacuum at 45-55° C. for 10 hours to give 25.68 kg (84.39% yield) of the title compound. HPLC purity is >99.9%.

EXAMPLE 4

The synthesis of 2-(3'-pyridyl)-1-hydroxy-ethylidene-1,1-bisphosphonic acid (I) monohydrate 48.6 ml (0.73 mol) of 98% methanesulfonic acid and 24.6 g (0.3 mol) of phosphorous acid are added into a flask. 21.3 g (0.15 mol) of phosphorus pentoxide is added in two portions to the obtained solution and is dissolved at 70-80° C. Then the reaction mixture is cooled to 40° C. and 13.7 g (0.1 mol) of 3-pyridylacetic acid is added. The obtained solution is aged at 80° C. for 48 hours and then at 100° C. for 24 hours. The mixture is cooled to 40-50° C., 48.6 ml of water is added dropwise and then the solution is stirred at 105-110° C. for 5 hours.

The mixture is cooled, neutralized with 60 g of 50% NaOH solution, cooled to 0-2° C. and stirred for further 2 hours. The precipitated product is filtered, washed with 2×20 ml of water and 20 ml of isopropanol, then recrystallized from water and dried to give 16.2 g (0.054 mol) of the title compound as monohydrate (54% yield). HPLC purity is >99.9%.

The invention claimed is:

1. A process for preparing a compound of the Formula (I)

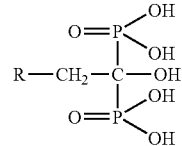

or a hydrate or a pharmaceutically acceptable salt or hydrate thereof in a purity of >99.9%, wherein
R is 3'-pyridyl or 2'-amino-ethylidene, which comprises the step of:
  phosphonylating a compound of the Formula (II)
  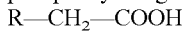
  R—CH$_2$—COOH
or a pharmaceutically acceptable salt or hydrate thereof in a reaction mixture with a chlorine-free phosphonylating agent comprising phosphorous acid in the presence of methanesulfonic acid and phosphorous pentoxide to obtain the compound of the Formula (I) or a hydrate thereof; and in the case where a pharmaceutically acceptable salt of the compound of the Formula (I) is desired, reacting the compound of the Formula (I) with a base.

2. The process for preparing a compound of the Formula (I) defined in claim 1 wherein the molar ratio of methane sulfonic acid: phosphorous acid: and phosphorous pentoxide in the chlorine-free phosphonylating agent ranges between 1 to 5: 1: 0.25 to 1.

3. The process for preparing a compound of the Formula (I) defined in claim 1 wherein the molar ratio of the compound of the Formula (II) and the phosphorous acid in the chlorine-free phosphonylating agent ranges between 1: 2 to 5.

4. The process for preparing a compound of the Formula (I) defined in claim 2 wherein the molar ratio of the compound of the Formula (II) and the phosphorous acid in the chlorine-free phosphonylating agent ranges between 1: 2 to 5.

5. The process for preparing a compound of the Formula (I) defined in claim 1 wherein the compound of the Formula (I) is isolated from the reaction mixture by hydrolyzing the compound of the Formula (I) with an equal volume mixture of water and methanesulfonic acid, followed by neutralization of the methanesulfonic acid with a base.

* * * * *